United States Patent [19]

Kondo et al.

[11] Patent Number: 4,740,458

[45] Date of Patent: Apr. 26, 1988

[54] REAGENT FOR ASSAYING CREATINE KINASE

[75] Inventors: Hitoshi Kondo; Masao Kageyama; Kosuke Tomita, all of Kyoto, Japan

[73] Assignee: Unitika Ltd., Hyogo, Japan

[21] Appl. No.: 784,432

[22] Filed: Oct. 4, 1985

[30] Foreign Application Priority Data

Oct. 5, 1984 [JP] Japan ................................ 59-210238

[51] Int. Cl.$^4$ .......................... C12Q 1/48; C12Q 1/50; C12Q 1/26; C12Q 1/54
[52] U.S. Cl. ........................................ 435/15; 435/17; 435/26; 435/810; 435/14
[58] Field of Search ................... 435/14, 15, 17, 26, 435/810, 832, 822, 188

[56] References Cited

U.S. PATENT DOCUMENTS

| | | | |
|---|---|---|---|
| 4,250,254 | 2/1981 | Modrovich | 435/17 |
| 4,277,562 | 7/1981 | Modrovich | 435/15 |
| 4,438,199 | 3/1984 | Miwa et al. | 435/14 |

FOREIGN PATENT DOCUMENTS 0095900  6/1984  Japan ................................ 435/14

*Primary Examiner*—Esther M. Kepplinger
*Attorney, Agent, or Firm*—Sughrue, Mion, Zinn, Macpeak & Seas

[57] ABSTRACT

A reagent system for assaying creatine kinase is disclosed. The reagent system consisting essentially of a first reagent comprising glucose-6-phosphate dehydrogenase, β-nicotinamideadenine dinucleotide (phosphate), and adenosine diphosphate, and a second reagent comprising creatine phosphate, said second reagent being maintained at a pH of from 7.5 to 10, and at least one of said first reagent and said second reagent containing glucokinase and glucose. The creatine kinase-assaying reagent exhibits remarkably improved stability in a dissolved state so that it can be prepared in large quantities and can be conventionally utilized to cope with urgent clinical examinations.

12 Claims, No Drawings

REAGENT FOR ASSAYING CREATINE KINASE

FIELD OF THE INVENTION

This invention relates to a reagent for assaying creatine kinase in body fluids, such as blood serum, urine, and the like.

BACKGROUND OF THE INVENTION

Creatine kinase (E.C. 2.7.3.2 registered in International Union of Biochemistry) is an enzyme present in muscular tissues throughout the body and in the brain. In the field of clinical examinations, an assay of creatine kinase activity is one of the important examinations usually carried out for diagnosis of cardiac diseases, e.g., myocardial infarction, muscular diseases, e.g., progressive muscular aystrophy, nervous diseases, central nervous system diseases, mental disorders, and the like.

Creatine kinase is an enzyme which catalyzes the reversible reaction shown by the following scheme (1) in both directions:

(1)

wherein ADP is adenosine diphosphate; and ATP is adenosine triphosphate.

Various methods have conventionally been proposed for assaying creatine kinase. One type of method comprises assaying the catalytic activity in the direction to the left of the above-described reaction (1). This type of method includes (a) a method of measuring an inorganic phosphoric acid released by hydrolysis of creatine phosphate, (b) a method comprising converting ADP to the oxidation of reduced from β-nicotinamideadenine dinucleotide (hereinafter abbreviated as NADII) by the action of pyruvate kinase and lactate dehydrogenase and measuring the decrease in absorption at 340 nm due to the oxidation of NADH, (c) a method comprising converting ADP to pyruvic acid by the action of pyruvate kinase and measuring hydrazone produced by the reaction between pyruvic acid and 2,4-dinitrophenylhydrazine, and the like. In recent years, however, scarcely has any of those methods been employed, due to their low sensitivity or unstable color development. On the other hand, a method for assaying the activity of creatine kinase in the direction to the right of the above-described reaction (1) includes (d) a colorimetric or fluorometric method in which creatine produced is reacted with a dye, (c) a method of using luciferase as disclosed in Japanese Patent Application (OPI) Nos. 41597/76, 26200/81 and 105199/82 (the term "OPI" herein used means "unexamined published application") and Japanese Patent Publication No. 5678/83, (f) a method of using phosphoglycrerate kinase and glyceraldehyde-3-phosphate dehydrogenase as disclosed in Japanese Patent Publication No. 34119/84 and Japanese Patent Application (OPI) No. 155000/81, (g) a method of using hexokinase and glucose-6-phosphate dehydrogenase, and the like. Of these, the colorimetric or fluorometric method (d) has poor reliability on the measured values; the luciferase method (e) requires expensive luciferase and a specific apparatus for measurement; and the phosphoglycerate kinase/glyceraldehyde-3-phosphate dehydrogenase method (f) is an absorption decreasing system similar to the pyruvate kinase/lactate dehydrogenase method as described above, and, therefore, involves the same disadvantages as associated with the pyruvate kinase/lactate dehydrogenase method and, in addition, requires use of phosphoglycerate kinase and glyceraldehyde-3-phosphate dehydrogenase that are more expensive than pyruvate kinase and lactate dehydrogenase. Hence any of the methods (d) to (f) is not satisfactory for practical use. The hexokinase/glucose-6-phosphate dehydrogenase method (g) has been employed most commonly because it is based on the most reasonable principle, exhibits satisfactory sensitivity and reproducibility and is capable of assaying a number of specimens. The principle of this assay method consists in the absorption increase at 340 nm due to the formation of reduced form β-nicotinamideadenine dinucleotide (phosphate) which is finally produced by the following reaction schemes:

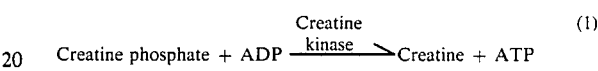
(1)

(2)

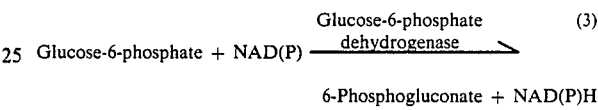
(3)

wherein NAD(P) is β-nicotinamideadenic dinucleotide (phosphate); and NAD(P)H is reduced form β-nicotinamideadenine dinucleotide (phosphate).

Ever since the first report on the hexokinase/glucose-6-phosphate dehydrogenase method by T.T. Oliver in *Biochem. J.*, Vol. 61, pp. 116–122 (1955), various improvements have been made. For example, there have been conducted studies on an assay method for inhibiting an activity of adenylic kinase that mainly exists in blood and causes a negative error in the hexokinase/glucose-6-phosphate dehydrogenase method, as described in U.S. Pat. No. 4,220,714, European Pat. No. 71087 (corresponding to Canadian Pat. No. 1,175,737), G. Szasz, W. Gerhardt, W. Gruber and E. Bernt, *Clin. Chem.*, Vol. 22, pp. 1806–1811 (1976) and G. Szasz, W. Gerhardt and W. Gruber, *Clin. Chem.*, Vol. 23, pp. 1888–1892 (1977); studies on thiol compounds for activation of creatine kinase as described in Japanese Patent Application (OPI) No. 106397/74 (DE 2302721) and G. Szasz, W. Gerhardt and W. Gruber, *Clin. Chem.*, Vol. 24, pp. 1557–1563 (1978); studies on the use of chelate compounds and stability of a reagent for assaying creatine kinase activity as described in G. Szasz, J. Waldenstrom, and W. Gruber, *Clin. Chem.*, Vol. 25, pp. 446–452 (1979); and the like. As a result, the hexokinase/glucose-6-phosphate dehydrogenase method has been established as the most reliable assay method for creatine kinase in clinical laboratories.

Nevertheless, the hexokinase/glucose-6-phosphate dehydrogenase method still has problems awaiting solution with respect to analytical accuracy and stability of a reagent for assaying creatine kinase. The former problem comes from the possible action of hexokinase on sugars other than glucose existing in body fluids, such as fructose and mannose, which results in a positive error of measured values. The latter problem is ascribed to the poor stability of the reagent during preservation in the form of a solution, i.e., a short working life of the reagent in a liquid state at room temperature (18° to 35° C.), even if a stabilizer, such as phycol (as described in Japanese Patent Application (OPI) No. 12897/77) and albumin, is added. Moreover, even in a so-called two-reagent system wherein the reagent is divided into two containers in a pH region of from 6.5 to 7.0, the stability of the reagent cannot be improved as desired so as to withstand use for a prolonged period of time in clinical laboratories. Therefore, satisfactory solutions to these problems have been strongly desired.

In order to overcome the above-described disadvantages encountered in the hexokinase/glucose-6-phosphate dehydrogenase method, a one-reagent system using glucokinase having extreme specificity to glucose and excellent heat stability has been described to be used in place of hexokinase, as disclosed in U.S. Pat. No. 4,438,199 (corresponding to European Patent Publication No. 43181A and Japanese patent application (OPI) No. 169598/81) and U.S. patent application Ser. No. 580,503 (corresponding to European Patent Publication No. 119722A and Japanese Patent Application (OPI) No. 151899/84). This glucokinase/glucose-6-phosphate dehydrogenase method also improves stability of a reagent for assaying creatine kinase in terms of preservation in a dissolved state at room temperature.

Although the glucokinase/glucose-6-phosphate dehydrogenase method somewhat resolved the problem of instability of the reagent after dissolution that was associated with the aforesaid hexokinase/glucose-6-phosphate dehydrogenase method, the stability of the reagent was still insufficient and a relatively large quantity of enzymes was required for maintaining the stability of the reagent for extended periods of time. In addition, with the recent increase of diseases that need urgent assays in clinical laboratories, such as myocardial infarction there has been a pressing demand for development of a reagent which enables accurate and rapid determination of creatine kinase activity in vital body fluids. In other words, high stability in the form of a solution for a long period of time has been required of a reagent so that creatine kinase activity can be assayed in any time of emergency without requiring adjustment of a reagent for minimizing measurement errors.

SUMMARY OF THE INVENTION

An object of this invention is to provide a reagent for assaying creatine kinase which is excellent in stability during preservation in the form of a solution.

As a result of extensive and intensive investigations for satisfying the above-described requirements, the present inventors have found that stability of a reagent for assaying creatine kinase after preparation can greatly be improved by preparing a first reagent comprising glucokinase, glucose-6-phosphate dehydrogenase, NAD(P), ADP and glucose and a second reagent comprising creatine phosphate, and maintaining the pH of the second reagent within a specific range.

It has also been found through further stucies that the stability of the reagent can further be improved by incorporating glucokinase and glucose in the second reagent in place of the first reagent, and thus reached the present invention.

That is, the present invention relates to a reagent system for assaying creatine kinase, consisting essentially of a first reagent comprising glucose-6-phosphate dehydrogenase, $\beta$-nicotinamideadenine dinucleotide (phosphate), and adenosine diphosphate, and a second reagent comprising creatine phosphate, said second reagent being maintained at a pH of from 7.5 to 10, and at least one of said first reagent and said second reagent containing glucokinase and glucose. The reagent system includes two preferred embodiments, i.e., a creatine kinase-assaying reagent system consisting essentially of a first reagent comprising glucokinase, glucose-6-phosphate dehydrogenase, NAD(P), ADP and glucose, and a second reagent comprising creatine phosphate, said second reagent being maintained at a pH of from 7.5 to 10, and a creatine kinase-assaying reagent system consisting essentially of a first reagent comprising glucose-6-phosphate dehydrogenase, NAD(P) and ADP, and a second reagent comprising glucokinase, creatine phosphate and glucose, said second reagent being maintained at a pH of from 7.5 to 10.

The creatine kinase-assaying reagent according to the present invention can be prepared and preserved in large quantities, and thus can promptly cope with urgent assaying requirements, since the reagent system has significantly increased stability in a dissolved state.

DETAILED DESCRIPTION OF THE INVENTION

Glucokinase which can be used in the present invention is not limited in source of supply, and includes glucokinase originated from microorganisms, e.g., *Aerobacter aerogenes*, animals, and the like. In particular, glucokinase produced by microorganisms whose optimum growth temperature ranges from 50° to 85° C. are preferred. Such microorganisms include, for example, the genus Bacillus, e.g., *Bacillus stearothermophilus, B. thermoproteolyticus, B. acidocaldarius*, etc.; the genus Thermoactinomyces; the genus Thermus; the genus Thermomicrobium; and the like. The preferred among these microorganisms is *Bacillus stearothermophilus*, and specific examples thereof ATCC 7933 (ATCC: The American Type Culture Collection, Maryland, U.S.A.), ATCC 7954, ATCC 8005, ATCC 10194, ATCC 12980, NCA 1503 (NCA: National Canners' Association, Washington, D.C., U.S.A.), UK 563 (FERM P-7275, deposited at Fermentation Research Institute, Agency of Industrial Science and Technology, Ibaragi, Japan, on Sept. 29, 1983), etc.

Glucose-6-phosphate dehydrogenase which can be used in the present invention is also not limited in source of supply, but it is preferable to use glucose-6-phosphate dehydrogenase which acts not only on NADP but also on NAD as a coenzyme, such as those originated from Leuconostoc mesenteroides, Pseudomonas fluorescens, etc.; and more preferably glucose-6-phosphate dehydrogenase originated from a thermophilic bacterium which acts on both NAD and NADP and is high in stability and preservability (as described, for example, in U.S. patent application Ser. No. 205,021, now abandoned (corresponding to Canadian Pat. No. 1,156,570 and Japanese Patent Application (OPI) No. 68391/81), and U.S. Pat. No. 4,331,762 (corresponding to Japanese Patent Application (OPI) No. 151491/81)).

Glucokinase and glucose-6-phosphate dehydrogenase can be prepared from the above-described sources by an appropriate combination of known techniques including extraction, purification, and so on, for example, a method of producing glucokinase as described in U.S. Pat. No. 4,331,762 and Japanese patent application (OPI) No. 91190/82, and a method of producing glucose-6-phosphate dehydrogenase as described in U.S. patent application Ser. No. 205,021, now abandoned (corresponding to Japanese patent application (OPI) No. 68391/81 and Canadian Pat. No. 1,156,570) and U.S. Pat. No. 4,331,762 (corresponding to Japanese Patent Application (OPI) No. 151491/81.

In the present invention, it is necessary to divide the reagent system that causes an enzymatic reaction of creatine kinase and participates in an enzymatic reaction leading to the production of NAD(P)H necessary for determination of UV absorption into a first reagent and a second reagent.

In one embodiment according to the present invention, the first reagent comprises glucokinase, glucose-6-phosphate dehydrogenase, NAD(P), ADP and glucose, and, in general, may further contain additives, such as an accelerator, an activator, etc. Such additives are conventional and include magnesium salts, e.g., magnesium acetate, magnesium sulfate, etc.; thiol compounds, e.g., N-acetylcysteine, glutathione, 2-aminoethylisothiouronium bromide, thioglycolic acid, cysteine, mercaptoethanol, dithiothreitol, dithioerythritol, etc.; sodium azide as an antiseptic; and the like. Besides, stabilizers, such as polysaccharides and derivatives thereof, e.g., soluble starch, methyl cellulose, carboxymethyl cellulose, etc.; proteins, e.g., albumin, $\gamma$-globulin, etc.; and water-soluble high polymeric compounds, e.g., polyvinyl alcohol, polyethylene glycol, etc., can also be used appropriately. The second reagent comprises creatine phosphate and may further contain known additives, such as sodium azide as an antiseptic.

According to another embodiment of the present invention, the first reagent comprises glucose-6-phosphate dehydrogenase, NAD(P) and ADP, and, in general, may further contain additives, such as an accelerator, an activator, etc. As the additives, any of those enumerated above for the first embodiment can be used. Further, all of the above-described stabilizers may also be used.

The second reagent comprises glucokinase, creatine phosphate and glucose, and may generally contain additives, such as an accelerator, an activator, etc. The additives that can be used are the same as those recited for the first embodiment. The same stabilizers as used in the first embodiment may also be employed.

In either of the first and second embodiments of the present invention, all components in the first reagent are dissolved in a buffer solution preferably having a pH of from 5.5 to 7.4. The buffer solution which can be used is not particularly restricted as long as it has a pH value of from 5.5 to 7.4, and includes, for example, imidazole-acetic acid, tris-acetic acid, triethanolamine-acetic acid, triethanolamine-NaOH, morpholinopropanesulfonic acid, morpholinoethanesulfonic acid, etc. Of these, the first four of the noted buffer solutions are more advantageous in the first reagent.

All components in the second reagent should be dissolved in a buffer solution of pH 7.5 to 10. The buffer solution which can be used is not particularly limited as long as it has a pH of 7.5 to 10, and includes, for example, tris-acetic acid, triethanolamine-NaOH, glycine-KOH, vicine, etc. Of these, the first two buffer solutions are used to advantage in the second reagent.

The concentration of the buffer solution for each of the first and second reagents can be selected so that a mixture of the first reagent and the second reagent in selected proportions may have an optimal pH value for creatine kinase to be assayed, i.e., of from 6 to 7.2. The first and second reagents are generally mixed in a volumetric ratio range of from 2/1 to 10/1, and preferably from 2/1 to 8/1. The concentration of the buffer solution each of the first and second reagents can be selected through simple experiments by fixing a mixing proportion to, e.g., 4/1 by volume; a pH of the first reagent to, e.g., 6.7; a pH of the second reagent to, e.g., 8.5; and a pH of the final reagent mixture to, e.g., 6.7 to 6.8. For example, the object can be achieved by using a 150 mM imidazole-acetic acid buffer solution (pH 6.7) for a first reagent and a 25 mM trisacetic acid buffer solution (pH 8.5) for a second reagent.

Specific examples of the first and second reagent formulations according to the first and second embodiments of this invention are shown below, but the present invention is not to be deemed to be limited thereto.

FIRST EMBODIMENT

First Reagent:
  Imidazole-acetic acid buffer solution
  Magnesium acetate
  Ethylenediaminetetraacetic acid (EDTA)
  ADP
  NAD(P)
  Adenosine monophosphate (AMP)
  Glucose
  Adenosine pentaphosphate
  N-Acetylcysteine
  Glucokinase
  Glucose-6-phosphate dehydrogenase
  Sodium azide
Second Reagent:
  Tris-acetic acid buffer solution
  Creatine phosphate
  Sodium azide

SECOND EMBODIMENT

First Reagent:
  Imidazole-acetic acid buffer solution
  Magnesium acetate
  EDTA
  ADP
  NAD(P)
  AMP
  Adenosine pentaphosphate
  N-Acetylcysteine
  Glucose-6-phosphate dehydrogenase
  Sodium azide
Second Reagent:
  Tris-acetic acid buffer solution
  Magnesium acetate
  EDTA
  Creatine phosphate
  Glucose
  Glucokinase
  Sodium azide The concentrations of each component for the creatine kinase-assaying reagent of the present invention can be selected according to known techniques. In general, from 0.1 to 40 unit/ml, and preferably from 0.2 to 20 unit/ml, of glucokinase; from 0.1 to 40 unit/ml, and preferably from 0.2 to 20 unit/ml, of glucose-6-phosphate dehydrogenase; from 2 to 70 mM, and preferably from 5 to 40 mM, of creatine phosphate; from 0.1 to 20 mM, and preferably from 0.2 to 10 mM, of ADP; from 0.05 to 20 mM, and preferably 0.1 to 10 mM, of NAD(P); from 1 to 200 mM, and preferably from 2 to 100 mM, of glucose; from 0.5 to 30 mM, and preferably from 2 to 15 mM, of a magnesium salt; from 0.5 to 50 mM, and preferably from 2 to 30 mM, of a thiol compound; from 0.2 to 20 mM, and preferably from 0.5 to 15 mM, of AMP; from 1 to 100 μM, and preferably from 2 to 50 μM, of adenosine pentaphosphate; from 0.1 to 20 mM, and preferably from 0.2 to 10 mM, of EDTA; and from 0.5 to 50 mM, and preferably from 1 to 30 mM, of sodium azide can be used.

According to the present invention, stability of the reagent system can be significantly improved by dividing the reagent components including glucokinase, glucose-6-phosphate dehydrogenase, NAD(P), ADP, glucose and creatine phosphate into two reagents and by controlling the pH value of the second reagent within a specific range. The thus improved stability makes it possible to prepare a large quantity of a reagent system at one time, thus providing an ability to cope with urgent clinical examinations. Further, the capability of preparing a reagent system in large quantities results in improvement of working efficiency and reduction of occurrences of discarding surplus reagent. Thus, the creatine kinase-assaying reagent in accordance with the present invention provides a very valuable contribution to the field of clinical examinations. Furthermore, the present invention has an effect on achieving a great saving of resources, since the amounts of enzymes and other expensive reagents required for assaying can be reduced.

The present invention will now be illustrated in greater detail with reference to Examples and Comparative Examples, but it should be understood that the present invention is not limited thereto.

EXAMPLE 1 AND COMPARATIVE EXAMPLE 1

A first reagent was prepared from 1.4 unit/ml of glucokinase produced by *Bacillus stearothermophilus* (manufactured by Seikagaku Kogyo Co., Ltd.), 1.2 unit/ml of glucose-6-phosphate dehydrogenase produced by *Leuconostoc mesenteroides* (manufactured by Oriental Yeast Industry Co., Ltd.), 1.25 mM of ADP disodium salt, 0.75 mM of NADP sodium salt, 25 mM of glucose, 6.25 mM of AMP, 12.5 μM of adenosine pentaphosphate, 12.5 mM of N-acetylcysteine, 12.5 mM of magnesium acetate, 10 mM of sodium, azide, 2.5 mM of EDTA, and 150 mM of an imidazole-acetic acid buffer solution (pH 6.7). Then, a second reagent was prepared from 100 mM of creatine phosphate, 10 mM of sodium azide, and 25 mM of a tris-acetic acid buffer solution (pH 8.5).

Both the first and second reagents were allowed to stand in a thermostat at 30° C., and the first reagent and the second reagent were mixed at a ratio of 4/1 by volume upon use to prepare a creatine kinase-assaying reagent for assaying creatine kinase activity in blood serum (Example 1).

For comparison, a creatine kinase-assaying reagent of one-reagent type was prepared from 3 unit/ml of the same glucokinase as used above, 3 unit/ml of the same glucose-6-phosphate dehydrogenase as used above, 1.0 mM of ADP disodium salt, 1.6 mM of NADP sodium salt, 20 mM of glucose, 5 mM of AMP, 10 μM of adenosine pentaphosphate, 10 mM of N-acetylcysteine, 10 mM of magnesium acetate, 10 mM of sodium azide, 2 mM of EDTA, 20 mM of creatine phosphate and 120 mM of an imidazole-acetic acid buffer solution (pH 6.7). The comparative reagent was allowed to stand in a thermostat at 30° C., and a requisite amount thereof was taken therefrom to assay creatine kinase activity in blood serum (Comparative Example 1).

A 0.5 ml portion of each of the thus prepared creatine kinase-assaying reagents kept at 30° C. was placed in a cell having a light path length of 1 cm, and 20 μl of a commercially available standard serum was added thereto. The creatine kinase activity of the specimen was assayed based on the change of absorbance at 340 nm by means of a spectrophotometer kept at 30° C. The creatine kinase activity obtained on the day of preparing the reagent (0 day) was taken as 100%, and changes in the assayed values with the passage of time were relatively traced while maintaining the reagents at 30° C.

The results obtained revealed that the creatine kinase activity could be substantially 100% detected over a period of 18 days from the day of preparing the reagent in Example 1, while, in Comparative Example 1, the creatine kinase activity could be substantially 100% detected over a period of only 10 days from the day of preparing the reagent.

The "days" used herein refers to a period (days) of the reagents used, i.e., a period that creatine kinase activity could be substantially 100% detected. Since the values to be obtained thereafter were an unreliable value, the reagents used were discarded.

It is apparent from these results that the stability of the reagent in the form of a solution can conspicuously be increased in accordance with the present invention by dividing the reagent into a first reagent and a second reagent and by controlling the pH of the second reagent. It can also be seen that reduction in requisite amounts of expensive reagents, such as glucokinase, glucose-6-phosphate dehydrogenase, NADP, etc., can be realized by the present invention.

COMPARATIVE EXAMPLE 2

A first reagent was prepared in the same manner as in Example 1. A second reagent was prepared from 100 mM of creatine phosphate, 10 mM of sodium azide and 25 mM of a tris-acetic acid buffer solution (pH 7.0).

Both the reagents were allowed to stand in a thermostat at 30° C., and the first reagent and the second reagent were mixed at a proportion of 4/1 by volume when in use to assay creatine kinase activity in blood serum in the same manner as in Example 1.

As a result, it was found that the creatine kinase activity could be substantially 100% detected over a period of only 12 days.

It can be seen from the above results that remarkable improvement in stability of the reagent after dissolution can be established as in Example 1 not only by dividing a creatine kinase-assaying components into two reagents but also controlling the pH of the second reagent within a specific range.

EXAMPLE 2

A first reagent was prepared from 1.2 unit/ml of glucose-6-phosphate dehydrogenase produced by *Leuconostoc mesenteroides* (manufactured by Oriental Yeast Industry Co., Ltd.), 1.25 mM of ADP disodium salt, 0.75 mM of NADP sodium salt, 6.25 mM of AMP, 12.5 μM of adenosine pentaphosphate, 12.5 mM of N-acetylcysteine, 10 mM of magnesium acetate, 10 mM of sodium azide, 2 mM of EDTA and 150 mM of an imidazole-acetic acid buffer solution (pH 6.7). Then, a second reagent was prepared from 100 mM of creatine phosphate, 10 mM of sodium azide, 10 mM of magnesium acetate, 2 mM of EDTA, 100 mM of glucose, 5.6 unit/ml of commercially available glucokinase (manufactured by Seikagaku Kogyo Co., Ltd.) and 25 mM of a tris-acetic acid buffer solution (pH 8.5).

Both the reagents were allowed to stand in a thermostat at 30° C., and were used to assay creatine kinase activity in blood serum in the same manner as described in Example 1.

As a result, 100% of the creatine kinase activity could be substantially detected over a period of 20 days from the day of preparing the reagent, indicating that incorporation of glucokinase and glucose in the second reagent further improves stability of the reagent after dissolution.

EXAMPLES 3 AND 4

Relative changes of creatine kinase activity with the passage of time were traced in the same manner as described in Example 1 (Example 3) or Example 2 (Example 4) except that the reagents were preserved at 4° C.

As a result, it was revealed that the creatine kinase activity could be substantially 100% detected over a period of about 60 days in Example 3 and about 70 days in Example 4.

EXAMPLE 5

The same procedures as in Example 2 were repeated except that the second reagent contained 150 mM of creatine phosphate.

As a result, the creatine kinase activity could be substantially 100% detected over a period of 24 days from the day of preparing the reagents.

While the invention has been described in detail and with reference to specific embodiments thereof, it will be apparent to one skilled in the art that various changes and modifications can be made therein without departing from the spirit and scope thereof.

What is claimed is:

1. A reagent system for assaying creatine kinase, consisting essentially of a first reagent comprising glucose-6-phosphate dehydrogenase, $\beta$-nocotinamideadenine dinucleotide (phosphate), and adenosine diphosphate, and a second reagent comprising creatine phosphate, said second reagent being maintained at a pH of from 7.5 to 10, and at least one of said first reagent and said second reagent containing glucokinase and glucose.

2. A reagent system for assaying creatine kinase as in claim 1, wherein said reagent system consisting essentially of a first reagent comprising glucokinase, glucose-6-phosphate dehydrogenase, $\beta$-nicotinamideadenine dinucleotide (phosphate), adenosine diphosphate, and glucose, and a second reagent comprising creatine phosphate, said second reagent being maintained at a pH of from 7.5 to 10.

3. A reagent system for assaying creatine kinase as in claim 1, wherein said reagent system consisting essentially of a first reagent comprising glucose-6-phosphate dehydrogenase, $\beta$-nicotinamideadenine dinucleotide (phosphate), and adenosine diphosphate, and a second reagent comprising glucokinase, creatine phosphate and glucose, said second reagent being maintained at a pH of from 7.5 to 10.

4. A reagent system for assaying creatine kinase as in claim 1, wherein the glucokinase is produced by a microorganism whose optimum growth temperature ranges from 50° to 85° C.

5. A reagent system for assaying creatine kinase as in claim 4, wherein the microorganism is selected from the genus Bacillus.

6. A reagent system for assaying creatine kinase as in claim 4, wherein said microorganism is a *Bacillus stearothermophilus*.

7. A reagent system for assaying creatine kinase as in claim 1, wherein the glucose-6-phosphate dehydrogenase is produced by *Leuconostoc mesenteroides*.

8. A reagent system for assaying creatine kinase as in claim 1, wherein the first reagent is maintained at a pH of from 5.5 to 7.4.

9. A reagent system for assaying creatine kinase as in claim 1, wherein the first and second reagents are provided in a volumetric ratio range of from 2/1 to 10/1.

10. A reagent system for assaying creatine kinase as in claim 1, wherein the first and second reagents are provided in a volumetric ratio range of from 2/1 to 8/1.

11. A reagent system for assaying creatine kinase as in claim 1, wherein the glucokinase is present in an amount of from 0.1 to 40 unit/ml, the glucose-6-phosphate dehydrogenase is present in an amount of from 0.1 to 40 unit/ml, the creatine phosphate is present in an amount of from 2 to 70 mM, the adenosine diphosphate is present in an amount of 0.1 to 20 mM, the $\beta$-nicotinamideadenine dinucleotide (phosphate) is present in an amount of from 0.05 to 20 mM, and the glucose is present in an amount of from 1 to 200 mM.

12. A reagent system for assaying creatine kinase as in claim 1, wherein the glucokinase is present in an amount of from 0.2 to 20 unit/ml, the glucose-6-phosphate dehydrogenase is present in an amount of from 0.2 to 20 unit/ml, the creatine phosphate is present in an amount of from 5 to 40 mM, the adenosine diphosphate is present in an amount of 0.2 to 10 mM, the $\beta$-nicotinamideadenine dinucleotide (phosphate) is present in an amount of from 0.1 to 10 mM, and the glucose is, present in an amount of from 2 to 100 mM.

* * * * *